United States Patent [19]
DeMeo

[11] Patent Number: 5,972,292
[45] Date of Patent: Oct. 26, 1999

[54] SEALING AND VENTING SYSTEM FOR OXIDATIVE DISINFECTION OF CONTACT LENSES

[75] Inventor: Gaetano DeMeo, Lomagna, Italy

[73] Assignee: Bausch & Lomb Incorporated, Rochester, N.Y.

[21] Appl. No.: 09/054,118

[22] Filed: Apr. 2, 1998

Related U.S. Application Data

[60] Provisional application No. 60/041,993, Apr. 16, 1997.

[51] Int. Cl.$^6$ ........................................................ A61L 2/18
[52] U.S. Cl. ................................ 422/25; 422/28; 422/30; 422/295; 422/297; 422/300; 422/301; 134/901; 206/5.1; 215/307; 220/366.1; 220/367.1
[58] Field of Search ..................... 422/292, 295, 422/297, 300, 301, 28, 30, 25; 215/307; 220/366.1, 367.1; 206/5.1, 205; 134/901

[56] References Cited

U.S. PATENT DOCUMENTS

| | | | |
|---|---|---|---|
| 4,637,919 | 1/1987 | Ryder et al. | 422/300 |
| 4,750,610 | 6/1988 | Ryder | 422/300 |
| 4,956,156 | 9/1990 | Kanner et al. | 422/301 |
| 5,011,661 | 4/1991 | Schafer et al. | 422/292 |
| 5,196,174 | 3/1993 | Cerola et al. | 422/300 |
| 5,366,078 | 11/1994 | Braun | 422/301 |
| 5,756,044 | 5/1998 | Mowrey-McKee et al. | 422/301 |

*Primary Examiner*—Terrence R. Till
*Assistant Examiner*—Fariborz Moazzam
*Attorney, Agent, or Firm*—Chris P. Konkol

[57] ABSTRACT

A lens case for disinfecting, cleaning, or storing contact lenses is described that provides a sealing and venting system for allowing the release of gas while avoiding liquid leakage. The venting means allows venting of gas when internal pressure increases, while maintaining a seal that is substantially gas and liquid-impermeable at other times. The lens case includes a cap securable to a container barrel and a mating cap. The venting of gas occurs via a tortuous-path mechanism resulting from appropriate surface roughness being produced on at least one of a pair of mating surfaces forming a seal between the cap and the container. In a preferred embodiment, a relatively roughened surface is produced on a cap flange that is in the shape of a circular lip downwardly extending from the inner surface of the cap. The mating surface of the cap flange sealingly presses against the rim portion of the container. The apparatus is particularly useful for the disinfection of contact lenses with hydrogen peroxide in which excess peroxide is decomposed into water and oxygen.

20 Claims, 5 Drawing Sheets

FIG. 5

SEALING AND VENTING SYSTEM FOR OXIDATIVE DISINFECTION OF CONTACT LENSES

This application claims the benefit of U.S. Provisional Application Ser. No(s). 60/041,993 filed on Apr. 16, 1997.

FIELD OF THE INVENTION

This invention relates to a lens case for holding contact lenses during a disinfection procedure in which a gaseous byproduct is liberated. In particular, the invention relates to an improved lens case for sealing solution and venting gas and to methods for making and using such a lens case.

BACKGROUND OF THE INVENTION

The proper maintenance of contact lenses requires periodic sterilization or disinfection to eliminate harmful bacteria and other microorganisms. A number of maintenance processes involve chemical reactions which involve the generation of gaseous by-products. For example, one conventional method of disinfecting contact lenses involves contacting them with a dilute solution of hydrogen peroxide. See, for example, U.S. Pat. No. 3,912,451 to Gaglia. By immersing a contact lens in a solution of hydrogen peroxide in a container, sterilization of the lens is relatively quickly accomplished.

Although hydrogen peroxide is highly effective in disinfecting contact lenses, hydrogen peroxide must be removed from solution in contact with the lenses prior to placing the lenses in a patient's eye, since the peroxides would otherwise cause eye irritation and patient discomfort. Typically, an agent for decomposing or "neutralizing" the peroxide into water and gaseous oxygen is present so that peroxide is reduced to a satisfactory level before the treated lens is removed from the solution in the container. The neutralizing agent typically may be a metal catalyst such as platinum or an enzyme such as catalase.

Because gaseous oxygen is produced by the neutralizing agent following oxidative disinfection it is necessary to avoid the buildup of excessive internal gas pressure in the container holding the lenses in solution. On the other hand, it is desirable that a lens case not allow indiscriminate leakage of liquid so that the peroxide solution does not escape from the container if the container is moved from the vertical or falls on its side. The container is, therefore, typically sealed to prevent liquids from being discharged from the container during the disinfection of the lenses and the neutralization of the disinfectant. A seal between the container and its cap should be designed to prevent spillage of liquid if the container falls on its side or is upset during transport. Typically, this means that when the pressure is near atmospheric pressure, little or no liquid can escape from the container even if held upside down.

In view of the need to both prevent the leakage of the disinfecting solution and to allow the discharge of gas when pressure builds up in the container, containers have been designed to provide a mechanism for the venting gases to the environment while otherwise maintaining a seal that is selectively resistant or impervious to the passage of liquids. Such venting mechanism is necessary in order to avoid risking fracture and/or explosion of the closed container.

A wide variety of venting and sealing means for lens cases have been developed for the above purpose. One approach has been to employ a gas-permeable, liquid-impermeable membrane having a porosity and/or hydrophobicity that allows gas but not liquid to escape from the lens case. For example, U.S. Pat. No. 4,396,583 to LeBoeuf discloses a vented case having a cavity in its cap for supporting a vapor-permeable, liquid impermeable barrier through which gas is vented. Similarly, Ryder et al. in U.S. Pat. No. 4,637,919 describes a contact lens cleaning container having a mating cap in which a filter assembly is positioned in a vent passageway. The filter assembly includes a hydrophobic membrane that continuously vents the gas generated within the container during the decomposition of peroxide. The pores in the hydrophobic membrane are sufficiently small to inhibit liquid leakage from the container while allowing the passage of gas under pressure.

U.S. Pat. No. 5,366,078 to Braun discloses a lens case having cap on the inner surface of which is positioned a hollow pedestal. Inside the hollow pedestal is sealingly positioned a hydrophobic impermeable gasket adjacent to an aperture in the top surface of the cap for discharging gas. The gasket fits snugly into the hollow pedestal and is provided with an aperture of sufficient dimension to discharge gas at an appropriate rate but small enough so that there is no significant discharge of liquid from the system even when the case is inverted or lies horizontally.

Another approach to venting lens cases has been to provide a deflectable gasket or diaphragm that resiliently deflects under pressure to allow the release of gas. For example, U.S. Pat. No. 4,956,156 issued to Kanner et al. discloses a disinfecting system which includes a cap having a bore in which a resiliently-deflectable diaphragm is sealingly positioned to prevent liquid leakage while allowing gas to pass when sufficient internal pressure develops to deflect the diaphragm. In particular, U.S. Pat. No. 4,956,156 discloses the diaphragm deflecting when the pressure exceeds 75 psia. Similarly, U.S. Pat. No. 5,250,266 issued to Kanner discloses a lens treating apparatus, including a container and a cap, in which gas is vented through a type of check valve in the cap. The check valve includes a disc having a linear slit therethrough. The slit generally provides a liquid-impermeable barrier, but when internal pressure is generated, the slit opens to allow gas to pass to the environment. In a slightly different approach, U.S. Pat. No. 4,996,027 issued to Kanner discloses a disinfecting system that comprises a self-reseating unitary gasket positioned between the cap and container of the device to provide a liquid-tight seal. Increased internal pressure during use causes the gasket to unseat at least partially, allowing gas to pass between the cap and container and to the environment.

A known disadvantage of the above venting mechanisms has been their complexity which increases their manufacturing costs. Efforts have been made to reduce the number of separably manufactured parts that need to be assembled in the cap. For example, U.S. Pat. No. 4,750,610 issued to Ryder discloses a disinfecting lens case having a cap that includes a resiliently deflectable flange which acts as a check valve in conjunction with the container rim. In operation, the cap flange is typically in a closed position, thereby preventing liquid leakage. When sufficient internal pressure develops, the cap flange deflects, allowing gas to pass through the loosely threaded container-cap connection to the outside of the container.

Another example of a deflectable venting means is disclosed in U.S. Pat. No. 5,558,846 to Alvord et al. Instead of a flange on the cap deflecting, the periphery of a container is designed to deflect. The cap includes a sealing rim adapted to mate with the periphery of the container at the open end of the container, thereby forming a primary sealing and venting means. When the pressure builds up to a certain point the during neutralization of the peroxide, the plastic at the top of the barrel deforms so as to release pressure. Secondarily, a hole in the cap positioned between the external periphery of the cap and the sealing rim allows gas to escape to the environment. The plastic then returns to the normal configuration when the pressure is below the deformation point. The plastic of the cap remains undeformed or rigid as this is happening. The proper flexing of the container periphery, therefore, depends on reduced strength in the container periphery relative to the cap sealing rim, preferably by reduced thickness relative to the sealing rim.

Alvord et al. state that, both from a manufacturing perspective and from an operational perspective, their device is less complicated than earlier devices that similarly involve resiliently deflectable parts. Since the sealing and venting means is an integrally molded part of the cap and container structure, additional parts are unnecessary.

One disadvantage of the venting mechanism described by Alvord et al. is that it is complicated to design, since the materials used for the container and cap, their properties, and the dimensions of various parts thereof can all affect the relative movement of parts. The materials and dimensions must be selected so that deformation of the container periphery consistently occurs under excessive pressure. Since the flexibility or other properties of the moving parts may change during use, consistency of venting and sealing may be difficult to achieve after extended use. Repeated movements of relatively rigid, highly stressed parts may result in structural fatigue or cracking. Since relatively high pressures are required to deflect the container periphery, there is a greater risk that a failure to vent for some reason, for example if the case fails to deform as expected, might result in the lens case exploding.

The previously described patents describe practical venting alternatives for peroxide-based lens cleaning/disinfecting devices. However, many of the prior systems involve relatively complex structures, increasing the cost of the device, as well as adding to the difficulty of manufacture. Other systems, while having fewer parts and being less costly to manufacture, require complicated engineering design to provide the required movement of certain parts based on material properties and carefully crafted dimensions. It would be desirable to obtain a lens case of simple design which vents gas without requiring extra parts such as membranes, diaphragms or gaskets and without depending on moving parts that must deflect or deform only after relatively high pressure builds up in the lens case. It is would be especially desirable to have a lens case that simply and reliably allows the venting of gaseous by-products without requiring the buildup of high or excessive pressure.

SUMMARY OF THE INVENTION

The invention is a lens case or vial container for disinfecting, cleaning, and/or storage of contacts lenses in a solution. In particular, the lens case provides for the venting of gases generated internally during treatment of the lenses in the lens case, while generally preventing the discharge of solution from the lens case during storage. The lens case of the present invention provides solution sealing and gas venting means that does not require additional components specific to the sealing and venting means such as separate membranes, diaphragms, or check valves that are designed to resiliently open under pressure. The lens case can, therefore, be manufactured with a minimum of parts and assembly steps. Consequently, the invention is especially suitable for a disposable lens case that is only intended to be used with an accompanying bottle of disinfecting solution.

The lens case is extremely safe to use. It provides for the initial release of gases at very low pressures and the maximum pressure attained in the lens case during typical use is relatively low. In a preferred embodiment, the excess gas exits the lens case through the entire circumferential region of the cap. Thus, venting does not depend on excessive pressures being relieved through a relatively small aperture that is subject to the risk of blockage.

The venting of gas occurs via a tortuous-path mechanism resulting from appropriate surface roughness being produced on at least one of a pair of mating surfaces forming a seal between the container and a securable cap. In a preferred embodiment, a relatively roughened surface is produced on a circular flange that downwardly extends from the inner horizontal surface of the cap. When the cap is attached to the container, the inner surface of the circular flange circumferentially presses against the top of the container along the perimeter of its rim.

The present apparatus is particularly useful for the disinfection of contact lenses with hydrogen peroxide in which the excess peroxide is decomposed into water and oxygen.

DETAILED DESCRIPTION OF THE INVENTION

As indicated above, the present invention relates to an improved sealing and venting means for a lens case used to hold one or more contact lenses during chemical treatment, especially during a disinfection regimen comprising a neutralization reaction involving the generation of a gaseous by-product.

While this invention is susceptible to embodiment in many different forms, there is shown in the drawings, and will be described herein in detail, one specific embodiment with the understanding that the following disclosure is to be considered an exemplification of the principles of the invention, and it is not intended to limit the invention to the embodiment illustrated.

Figure 1:
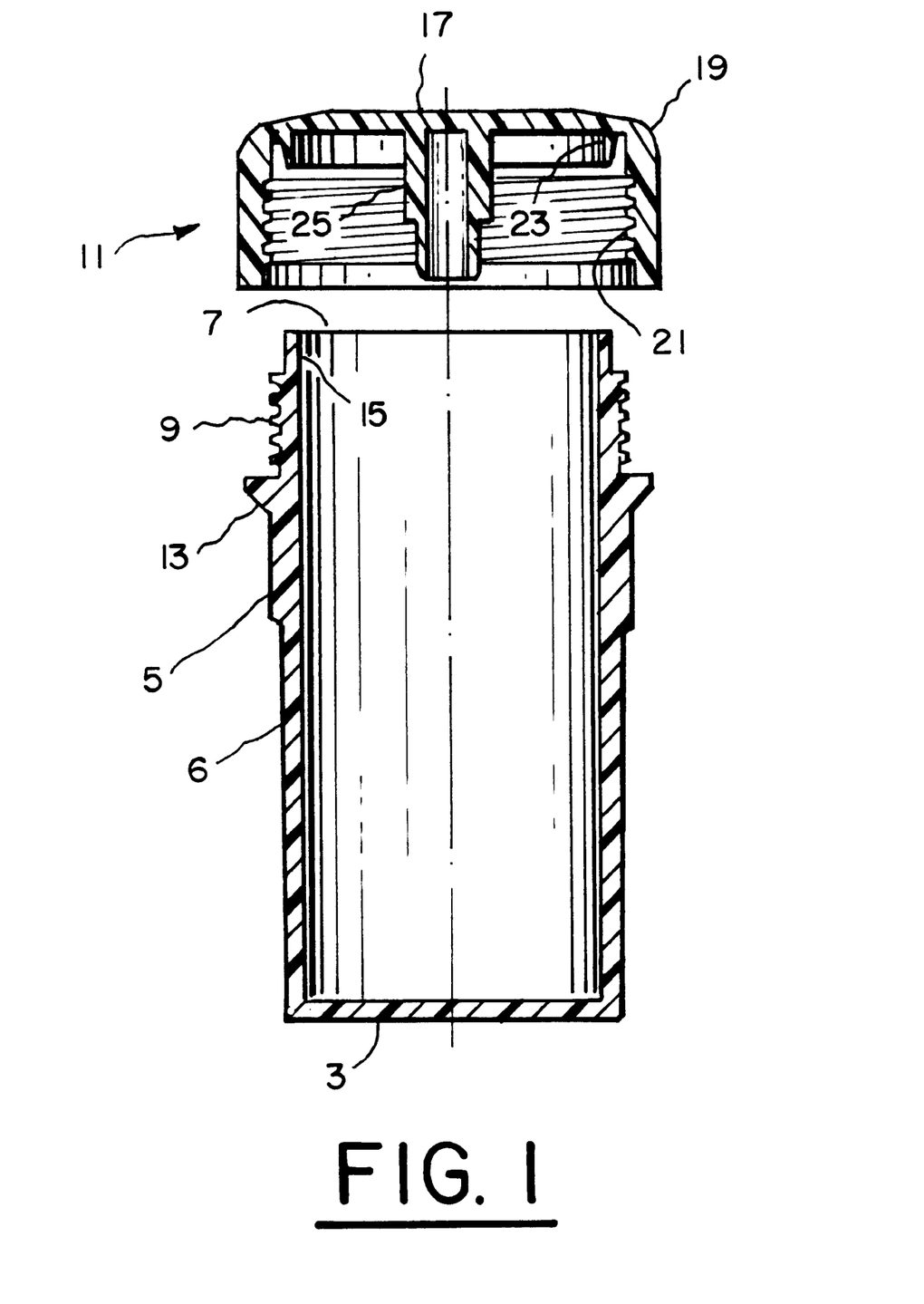
FIG. 1 is an exploded cross-sectional view of the lens case of the invention, including the container and the cap (absent the lens holder).

FIG. 1 shows a preferred embodiment of a lens case according to the present invention which comprises a container 1 having bottom wall 3, side walls 5, and opening 7 at the top. The container is preferably made of a translucent or transparent material, and may have surface ornamentation, for example, a fluted design resulting from a parallel series of vertically extending indentations 6 in the external surface of the side walls such that a scalloped surface is shown in cross-section. External threads 9 near the top of the container provide a means of engagement for a cap 11. Below the threaded portion of the container, a ledge 13 extending around the outside perimeter of the container may be used to limit the distance the cap may be threaded onto the container and/or the amount of force that may be applied in tightening the cap. An annular rim portion 15 is positioned above the external threads. The inside perimeter of the container at the top of the annular rim portion defines the circular opening 7.

The cap 11 comprises top wall 17, side walls 19, and internal threads 21 by which the cap is securable to the container 1, the internal threads 21 being complementary to the external threads 9 on the container. Threading is the preferred means of releasable affixing the container to the cap. The cap 11 further comprises a vertical flange or sealing lip 23 that downwardly extends from the inner surface of the cap. The sealing lip 23 is intended to press against the inner surface of the annular rim portion 15 of the container when the lens case is closed. Finally, a hollow substantially cylindrical protuberance 25 extends downward from the inner surface of the cap for attaching the lens holder, as will be explained below.

Tile container 1 is of sufficient capacity to submerge a pair of contact lenses in a desired amount of liquid treating solution, such as a disinfecting solution of hydrogen peroxide, when the contact lenses arc held in a lens holder attached to the cap. (The lens holder is shown unattached and disassembled in FIGS. 2 and 3.) A conventionally shaped catalytic element may be fixedly held at the bottom of the container by means of a suitably dimensioned rectangular tab or cylindrical post means projecting perpendicularly from the inside surface at the bottom of the container. Such a tab or post may be integrally molded onto the bottom surface of the container. The catalytic element may be molded in the form of a split ring that grips the post by means of a friction fit. See, for example, U.S. Pat. No. 4,011,941. Alternatively, the catalytic element may be fixedly or removably attached to a tab at the bottom of the lens holder as disclosed in U.S. Pat. No. 5,558,846.

The container may be formed from a wide range of plastic materials, preferably a transparent material, including without limitation, hydrophobic polymeric materials such as styrene butadiene, polyethylene, polypropylene, or the like. The cap and the sealing lip may be formed from the same material as the container or from a different material. A preferred material for the cap is Nuvolens® polyproplene and a preferred material for the container barrel is Stirolux® styrene butadiene, both materials available from BASF, Inc.

While the dimensions of the container body are not crucial to the invention, the container body preferably has a cylindrical shape and a thickness ranging from about 1 mm to about 5 mm. While the sealing lip 23 of the cap may have a wide variety of shapes and dimensions, it is preferably in the shape of an elongated rectangle with the side facing the rim of the container being at a slight angle from the side wall and having a rounded distal edge. Preferably, the thickness of the cap sealing lip at its base, near the inner surface of the cap, is about 1 to 3 mm, more preferably about 1.0 to 2.5, most preferably about 1.7 mm.

When assembled, the cap further includes a lens holder affixed thereto in an orientation such that said lens holder is positioned within said container when said cap is affixed to said container. The lens holder comprises a lens supporting means cooperating with a pair of lens retaining means. The lens supporting means comprises a mounting post for attachment at one end to the inner surface of the cap. The other end of the mounting post leads to a generally rectangular submergible body that includes on each side a convexly projecting lens-shaped surface for receiving and supporting each of a pair of contact lenses. The two retaining means each comprise a basket or cage structure and are pivotally mounted on opposite sides of said submergible body, for securing said lenses adjacent said lens shaped surfaces. The elements making up the lens holder are constructed to allow a pair of contact lenses to be supported in a relatively fixed or limited position in the lens case of the present invention, wherein the lens holder is suspended and sealed within the lens case while submerging the lenses in solution, so that the lens case can be utilized for sterilizing a pair of lenses as well as storing them when they are not in use.

There are numerous conventional variations of lens holders, for example, as described in U.S. Pat. No. 3,770,113, U.S. Pat. No. 4,011,941, U.S. Pat. No. 4,396,583, U.S. Pat. No. 4,956,156, U.S. Pat. Nos. 4,996,027, and 5,366,078 which are all hereby incorporated by reference. The present invention is not limited to the particular structure or components required for holding the lens. However, a preferred lens holder will be described in order to disclose the best mode of the present invention.

Figure 2A:
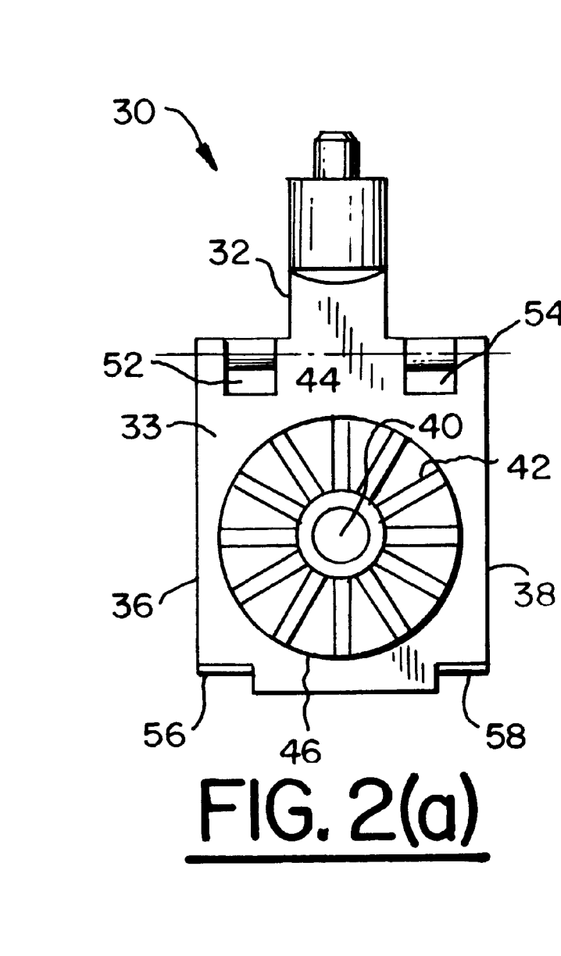
FIG. 2(a) shows a front view of the lens supporting means in the lens holder.
Figure 2B:
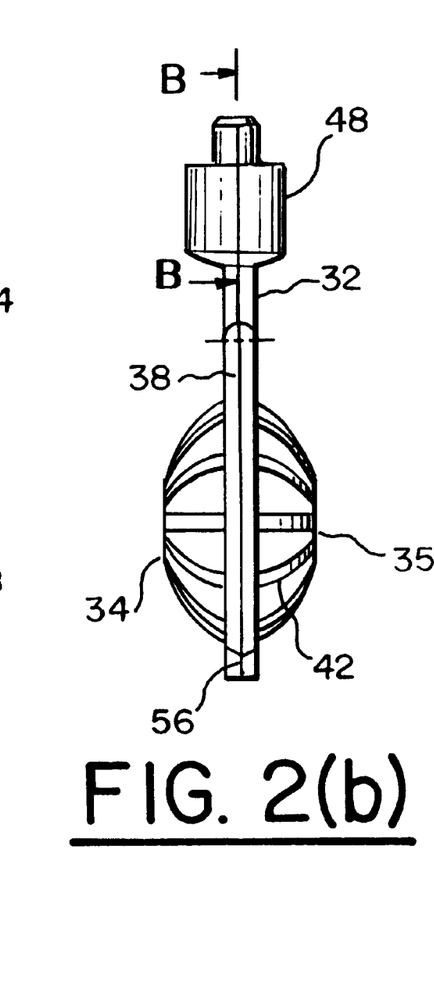
FIG. 2(b) shows a side view of the lens supporting means.
Figure 2C:
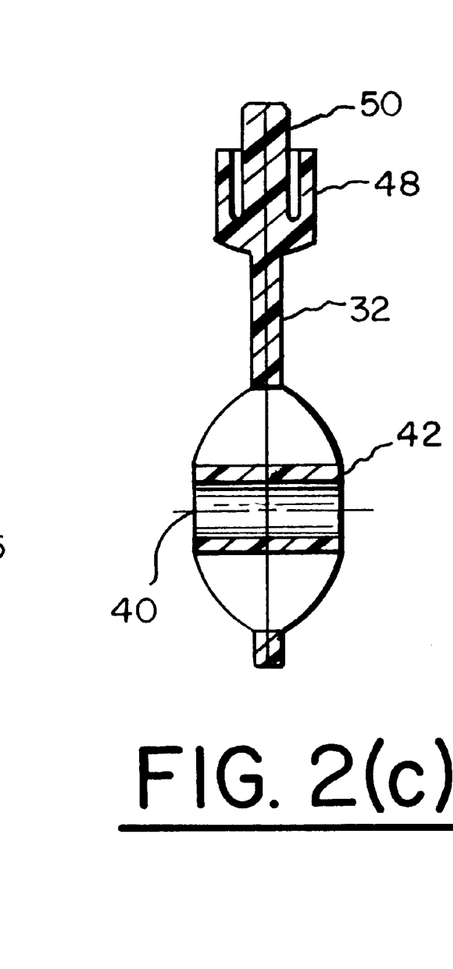
FIG. 2(c) shows a cross-sectional side view of the lens supporting means.

Referring now to FIGS. 2(a) and 2(b), a front and side view of the lens supporting means is shown, with a cross-sectional side view of the supporting means shown in FIG. 2(c). The lens supporting means 30, sometimes referred to as the pedestal, comprises a mounting post 32 leading to a submergible body 33 having lateral edges 36 and 38 and comprising convex surfaces 34 and 35 on opposite sides of the principal sides of the submergible body. A central tubular passageway 40 with radial fins 42, roughly forming a pointed or elongated semispherical shape, extending from the tubular wall 44 of the tubular passageway to the inner surface of the circular wall 46 cut or molded in the submergible body 33 of the supporting means. A plug means 48 at the end of the mounting post 32 is designed with an annular groove 50 for fittingly engaging with the cylindrical protuberance 25 on the cap. Two rectangular apertures 52 and 54 near the upper edge of the submergible body are designed to provide a means for attaching the hinge arms of the lens baskets. The apertures have rounded bearing surfaces at the upper inside surface of the apertures for cooperation with curved inside surfaces of the hinge arms on the retaining means, as described in greater detail below. Two triangularly beveled edges 56 and 58 are designed to clickingly engage with a latch arm on each of the lens baskets, as will now be described.

Figure 3A:
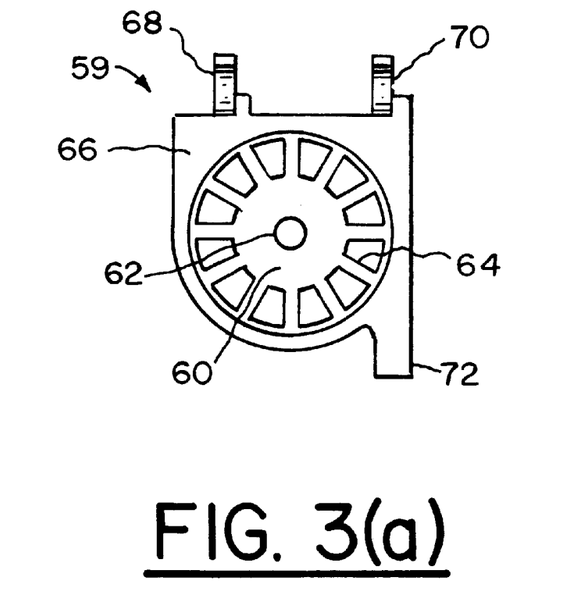
FIG. 3(a) shows a front view of a lens retaining means, including a lens basket, in the lens holder
Figure 3B:
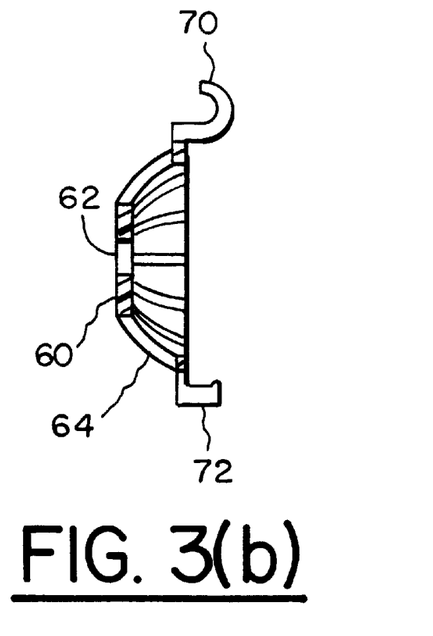
FIG. 3(b) shows a side view of the lens retaining means.

Referring now to FIGS. 3(a) and 3(b), a front view and side view, respectively, of a lens retaining means 59 is shown comprising a lens basket or cage having a disk-shaped medallion 60 supporting a plurality of spokes or ribs 64 which radially extend from the medallion to the periphery of a circular opening in a surrounding frame structure 66 of the lens retaining means. The medallion has an opening 62 for allowing the flow of liquid over the lens held under the retaining means. The medallion may have a surface design to indicate which lens, the left or right, is placed in thereunder. A pair of curved hinge arms 68 and 70 extends from the upper edge of the frame structure 66 and a latch arm 72 extends from the lower edge of the frame structure. The pair of lens retaining means are identical. The retaining means is pivotally mounting on each side of the supporting means by means of the hinge arms inserted in the apertures 52 and 54 in the lens supporting means.

In operation, after a lens is placed on the convexly shaped surface of the supporting means, the retaining means is snapped into a closed position on the beveled edge of the supporting means. The lens is thereby captively disposed within a caged area defined by the relevant portions of the supporting means and retaining means. The procedure is repeated with the other lens on the opposite side of the lens holder. It is noted that the ribs in the retaining means line up with the fins in the supporting means such that pie-shaped open sections are visible to the observer looking along a central axis extending through the front of the basket. Also, the aperture in the medallion in the retaining means lines up with at least a portion of the tubular passageway in the supporting means such that a hole extending all the way through the center of the basket is also observable along the central axis. Preferably, 12 ribs in each retaining means and 12 fins in the supporting means are employed.

Figure 4:
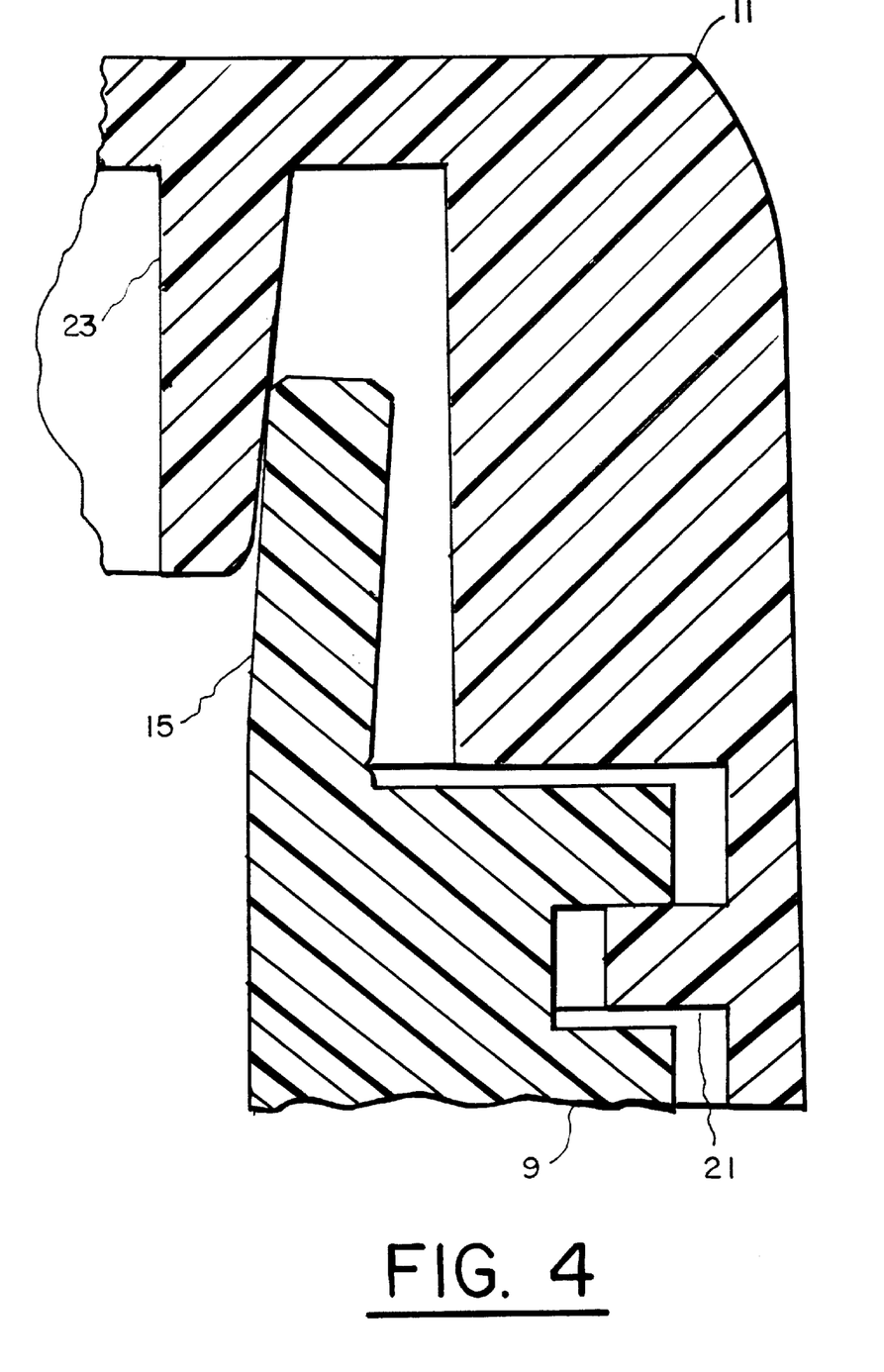
FIG. 4 shows an enlarged sectional view of the venting means shown in FIG. 1 illustrating the mating surfaces that seals the internal chamber of the lens case.

FIG. 4 shows an expanded view of the venting means of FIG. 1 in which a seal is formed between the sealing lip 23 in the cap 11 and the annular rim portion 15 of the container. As shown in the Figure, the two parts press against each other when the lens case is closed. When the complementary threads 9 and 21 on the container and cap, respectively, are fully and securely engaged, the outer mating surface of sealing lip 23 presses against the inner mating surface of the annular rim portion of the container, wherein the terms "inner" and "outer" refer to whether the surface is facing inwardly or outwardly to the central axis of the lens case, container, and cap. In other words, the internal diameter of the container and annular rim portion 15 is slightly less than the external diameter of the sealing lip 93, resulting in an interference fit that creates a liquid impervious seal.

While not wishing to be bound by theory, it is believed that, as the sealing parts initially contact each other when affixing the cap onto the container barrel, the end of the container rim portion rounds the rounded end of the sealing lip and slides onto the flat region of the sealing lip until the threads stop the motion after about 1 to 5 mm of vertical barrel motion. The rim portion 15 deforms slightly. This is because the contact point is at the end of the rim portion causing greater moments to be generated in the rim portion than in the sealing lip of the cap. A typical contact region is, for example, about 0.25 mm wide below the tangency point of the upper end of the rim portion and the vertical surface of the sealing lip. The amount of contact pressure may vary over the contact zone. Significant pressure between the parts is maintained at all internal gas pressures. For example, in one particular embodiment, the peak contact pressure was calculated to vary from about 1000 to 2000 psi, based on finite element analysis. Thus, the contact pressure creates a relatively liquid-impermeable seal by means of pressing engagement between the mating or contacting surfaces shown in FIG. 4.

As pressure in the case exceeds atmospheric pressure, the gas "leaks" out between the seal formed between the container and the cap due to microchannels formed between the mating surfaces of the sealing lip and the rim portion. The roughness of the plastic surfaces in the contact zone dictates the release of pressure. The microchannels created by the roughened surface provides a network of tortuous paths by which gases escape through the seal.

By changing the roughness of the molding tool employed to make the cap, the roughness of the mating surface on the sealing lip, which forms the seal with the rim portion of the container, can be controlled. The roughness of the tool can be adjusted employing conventional techniques such as chemical erosion, electrical discharge, vapor hone, sandblasting or the like. Electrical discharge machinery (EDM) employing conventional equipment is the preferred means for roughening a surface of the tool, either during the manufacture of the tool or afterwords. The roughnesses can be quantified by root mean square (RMS) roughness, a value that may be determined by Atomic Force Microscopy (AFM). An alternative scale, referred to as the Charmilles scale, is correlated in the Examples below to the RMS roughness in microns.

As surface roughness increases, the relative number and size of microchannels increases and gas venting increases. The roughened surface on the mating surface of the sealing lip is obtained by adjusting the corresponding roughness of the tool used to form the surface to an RMS roughness that is suitably at least about 0.5 microns, preferably by adjusting the roughness of the tool used to form a contacting or sealing surface in the cap and/or container to an RMS roughness of between about 0.5 microns and 50 microns, more preferably between about 3 to 20 microns, and most preferably between 5 and 10 microns. In general, the lower limit of the roughness is determined by the degree of roughness that just allows sufficient venting of the gas, and the upper limit of the roughness is determined by the degree of roughness that just prevents the liquid from escaping due to the miniscus level or surface tension of the solution.

The desired surface roughness on the tool employed in making the cap of the lens case can be determined by measuring the maximum gas pressure within the capped lens case during a disinfecting regimen. The roughness of the tool, and correspondingly the surface of the sealing lip, is preferably adjusted so that the container does not exceed a predetermined pressure above atmospheric pressure. Suitably, the maximum pressure reached in the lens case is under about 20 psi, preferably 1 to 10 psi, more preferably about 1 to 5 psi, and most preferably not more than about 2.0 psi above atmospheric pressure. Similarly, it is preferable that the lens case begin to vent gas at pressures below 5 psi, preferably at or below about 1 psi above atmospheric. It is noted that the surface of the tool is typically of greater roughness than the surface of the sealing lip it produces, but the roughness of the tool is more readily measured and reliably produces a given surface roughness.

Alternatively, the mating surface on the container or the mating surfaces on both the cap and container that form the cap-to-container seal or can be roughened to provide microchannels for tortuous path venting of pressurized gases, in which event, the tool for molding the container is appropriately roughened.

Once the gas exits from the lens case through microchannels formed by the roughened surface in the sealing lip, the gas may escape to the environment via a variety of subsequent venting means. For example, the gas may escape through a loosely-fitted thread connection between the container and cap. Other ways of venting the gas beyond the container-cap seal is by means of one or more openings in the cap. The openings may be positioned through the cap, at points between the sealing lip of the cap and the outer periphery of the cap. The size of the opening is preferably large enough to avoid debris or other blocking agents from easily obstructing the opening and inhibiting proper venting. A suitable diameter for the opening is about 0.25 to 5 mm. Preferably, however, the gas escapes to the environment through the interfacial space between the threaded surfaces of the cap and container, the threading being sufficiently loosely mated to provide a pathway to the environment. This has the advantage that the gases are discharged to the environment over an extended interfacial area so that it is less likely that pressure can build up by inadvertent blockage of the gases at one spot in the route of venting.

The present invention is relatively simple to design and manufacture. In manufacturing the lens case of the present invention, no other parts must be molded for the venting system other than the cap and the container. Thus, for example, both the cap (including sealing lip and threads) and container may be formed by injection molding, without additional processing.

The venting, means of the present invention is produced without the operation of complicated mechanical action or, in fact, any moving parts at all. More complex mechanical venting systems may fail for a number of reasons, such as corrosion, material fatigue, cracking, etc.

A liquid-impermeable seal is established by integral components of the cap and container, while gas venting is allowed by a predetermined roughness on at least one of the mating surfaces of the container or cap, preferably the cap. Since the material properties and dimensions do not need to be designed to open or move a valve, additional dimensions of freedom in the selection of materials and in the degree and rate of venting based on surface roughness are possible.

Thus, another embodiment of the present invention provides an improved method of providing a contact lens treatment apparatus with a sealing and venting means. Generally, the method involves providing a cap with a sealing lip on the side of the cap adapted to mate with said container, in which the sealing lip has a predetermined roughness that provides microchannels for passage of gas under pressure. The appropriate surface roughness can be determined by measuring the maximum pressure obtained in the lens case during the disinfecting regimen, in general the greater the roughness, the greater the venting, as demonstrated in the Examples below. In addition, the method involves forming a means for allowing gas to continuously vent to the environment after passing through the microchannels in the sealing means, preferably through the space between threads in the cap and container. Thus, in the preferred embodiment, as previously discussed, the venting area always extends over a wide circumferencial area which is difficult to obstruct.

In another aspect of the present invention, a disinfection regime is carried out in the lens case as follows. A hydrogen peroxide solution is introduced into the container, which solution suitably comprises hydrogen peroxide in an amount of between about 1 and 5 percent by weight, preferably about 2.5 to 3.5 percent, more preferably about 3 percent by weight. Typically, the solution further comprises a peroxide stabilizer and sufficient sodium chloride or its equivalent to yield an 0.85% saline solution. A pair of contact lenses, held within the lens holder of the lens case, is then immersed in the solution while the lens case is closed. The lenses are allowed to remain in contact with the hydrogen peroxide for a sufficient period of time, typically at least about 6 hours, to disinfect the lenses and neutralize the hydrogen peroxide with a catalyst which is fixedly submerged in the solution. After this time, the lenses are effectively sterilized and the concentration of peroxide is reduced to less than 100 ppm, preferably less than 50 ppm, more preferably about 25 ppm or less. Subsequently, the lens may be optionally rinsed with an isotonic saline or cleaned and rinsed with a conventional solution.

EXAMPLE 1

A mathematical model of the venting means in a sample lens case according to FIGS. 1 to 4 was constructed using finite element analysis. Based on dimensional information and plastics properties, the model was used to determine the behavior of the lens case at various internal pressures. A five-degree wedge of the upper part of the lens case, including the cap and upper portion of barrel, was constructed of solid element in MSC/NASTRAN software. Symmetry conditions were used to mimic the rest of the upper part of the lens case. Frictionless contact was assumed between the inner diameter of the upper rim portion of the barrel and the outer diameter of the sealing lip. While the cap was assumed to be made of Nuvolens® polypropylen plastic ($E=0.104$ N/mm$^2$, $v=0.3$) the barrel was assumed to be fabricated out of Stirolux® styrene butadiend plastic ($E=0.18$ N/mm$^2$, $v=0.38$), wherein E is the modulus and v is the Poisson's ratio. While the cap was held fixed at the threads, the displacement of the barrel was enforced at the corresponding barrel thread surfaces. The total enforced displacement was assumed to be enough to fully screw the threads. This displacement was between 1.9 and 1.95 mm after initial contact between the two parts. The contact zone was calculated to be a 0.25 mm wide region below the tangency point of the barrel rim radius and the vertical surface of the sealing lip.

Using, the mathematical model, a 1.0 psi pressure was applied to the inside of the barrel/cap assembly to simulate the build up of gas released during the disinfection process. The effect on the contact stresses between the inner diameter of the upper rim portion of the barrel and the outer diameter of the sealing lip was examined. The contact pressure distribution shows very singular behavior ramping up from 74.0 psi at the lower edge of the contact region to nearly 2000.0 psi at the start of the radius. A 1.0 psi gas pressure has negligible effect of the contact pressures at the lip of the barrel. The pressure of the gas was then increased.

Figure 5:
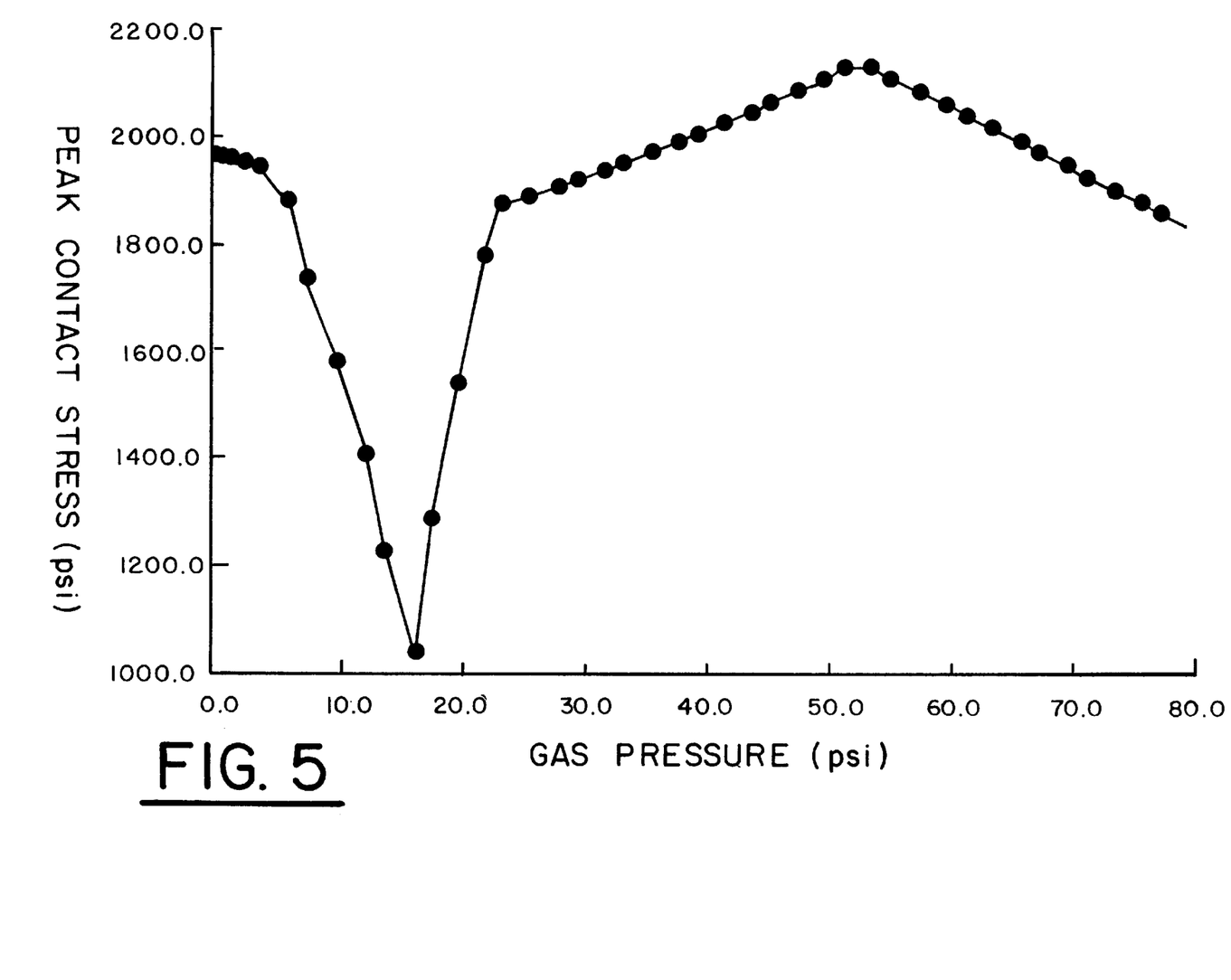
FIG. 5 shows a graph of the peak contact stress versus gas pressure for the sealing means which graph is based on a finite element analysis.

FIG. 5 shows how the peak contact pressure changes as the gas pressure is further increased inside the fully tightened parts. At first the contact pressure drops due to pressure applied to the barrel and the cap. Vertical pressure on the cap causes upward motion and rotation of the cap seal relieving the contact stress between the two parts. However, a second simultaneous behavior causes the contact stress to rise again. The geometric rotation of the cap seal causes less area to remain engaged between the two parts. This concentrates the contact load higher on the barrel lip as pressure increases. Once this contact area has stabilized at around 53.0 psi, the contact stress begins to drop again. However, even after 80.0 psi of gas pressure there is still significant contact pressure between the two parts. This shows that the mating surfaces of the cap-to-container seal are maintained in constant contact at all pressures and that the venting of the gas must occur through microchannels between mating surfaces in accordance with a tortuous path mechanism.

EXAMPLE 2

This example illustrates the dependency of venting in accordance with the present invention on the roughness of the plastic surface forming the seal. By changing the roughness of the tool producing the cap, the roughness of the sealing lip on the cap which forms the seal with the barrel was controlled. The various samples prepared had cap roughnesses corresponding to a tool roughness of 0, 30, 36, and 39 on a Charmilles scale wherein 0 is the smoothest and the higher the number, the rougher the surface. The Charmilles scale was created by an equipment vendor of the same name. The Charmilles scale varies from 0 to 100 where 0 is the smoothest and the higher the number, the rougher the surface. The correlation between the Charmilles scale and RMS roughness in microns is shown in Table I below:

TABLE I

| Charmilles Scale | 0 | 12 | 15 | 18 | 21 | 24 | 27 | 30 | 33 | 36 | 39 | 42 | 45 |
|---|---|---|---|---|---|---|---|---|---|---|---|---|---|
| RMS Roughness (microns) | 0 | 0.40 | 0.56 | 0.80 | 1.12 | 1.60 | 2.24 | 3.15 | 4.50 | 6.30 | 9.00 | 12.5 | 18.0 |

The various caps were attached via connectors and gaskets to an Thommen Mod. HM28 manometer and computer for the determination of pressure versus time. A conventional peroxide regimen was run following placement of platinum catalyst disc at the bottom of the lens case, and filing the lens case with 9.7 ml of Bausch & Lomb One Sept® peroxide solution. The gas pressure curve was followed through the 6 hour regimen time for each sample. Each pressure curve rose until a maximum pressure was achieved, venting occurred, and the pressure curve decayed over time back to a baseline. Ten samples at each roughness were tested. The average maximum pressure achieved during the peroxide regimen for the various surface roughnesses are shown below in Table II:

TABLE II

| Charmilles Scale Tool Roughness | 0 (Smooth) | 30a | 30b | 36 | 39 |
|---|---|---|---|---|---|
| Max Pressure (psi over atm) | 40.0 | 9.5 | 8.3 | 1.3 | 0.5 |

Sample 30a was tightened at 10 inch-pounds and sample 30b was tightened at 5 inch-pounds, measured with a spring torque tester having a 0–25 lbs scale. All other samples were tightened at 5 inch-pounds. The cap systems with a tool roughness of 36 and 39 on the Charmilles scale returned to baseline pressure within about 10 minutes, and the systems with a tool roughness of 30 returned to baseline within 20–40 minutes. The systems with 0 tool roughness did not return to baseline pressure over the 6 hour regimen time.

Obviously, the higher the pressure attained in the lens case, the lower the venting capacity. The results show that the venting of oxygen is higher as the roughness of the tool and cap increases, demonstrating that pressure build-up is inversely proportional to surface roughness. As roughness increases, the venting between the cap and the barrel plastic increases and the system will vent at lower pressures. This experiment also demonstrates a tortuous path venting mechanism, since the roughness of the plastic would not be a significant factor for a venting mechanism based on the discharge of excess gas based on plastic deformation. If a plastic deforms at 8–10 psi (cap 30) then the pressure should never achieve 40 psi (cap at 0 roughness) as the plastic would deform at the lower pressure. As roughness increases, the microchannels increase in number and size and will collectively vent at lower pressures.

EXAMPLE 3

This Example illustrates a determination of the minimum pressure at which gas vents from a lens case in accordance with the present invention. Sample lens cases connected to a source of pressure were closed using a torque indicator set at 3 in lbs, 5 in lbs, and 8 in lbs. Each lens case was submerged under water and the pressure necessary to cause internal air venting or leakage, as observed by bubbles escaping the caps, was recorded with a pressure gauge having a tolerance of +/−0.45 psi. For each sample lens case, the internal pressure at which leakage occurred was about 1 psi above atmospheric pressure. This shows that the seal was able to provide initial venting of gas at very low pressure, consistent with a tortuous path mechanism that is safe and reliable.

The invention has been described in detail, with reference to certain preferred embodiments, in order to enable the reader to practice the invention without undue experimentation. However, a person having ordinary skill in the art will readily recognize that many of the previous components and parameters may be varied or modified to a certain extent without departing from the scope and spirit of the invention. Accordingly, the intellectual property rights to this invention are defined only by the following claims.

What is claimed is:

1. An apparatus for treating ophthalmic lenses, wherein said apparatus is capable of venting internal gas, comprising:
   (a) a container for receiving a treating solution, said container having a horizontal bottom wall, vertical side walls, and an open end defined by an annular rim portion of the side walls;
   (b) a removable cap affixed to said container at said open end, said cap having a sealing lip downwardly extending from the inner surface of the cap, which sealing lip comprises a first mating surface overlapping and pressingly engaging a complementary second mating surface on the annular rim portion of the container when the cap is fully affixed to the container, thereby providing a closed disinfecting chamber that is selectively sealed to prevent the discharge of solution, wherein at least one of the first and second mating surfaces is sufficiently roughened to allow gas to escape from the disinfecting chamber when the internal pressure exceeds a predetermined pressure above atmospheric pressure such that the maximum pressure attained in the lens case is below about 20 psi above atmospheric pressure, and wherein said apparatus further includes a subsequent passage means for allowing gas passing from said disinfecting chamber between said mating surfaces to exit to the environment; and
   (c) a contact lens holder attached to the inner surface of the cap for retaining a pair of lenses in a submerged location within the apparatus when the cap is affixed to the container.

2. The apparatus of claim 1 wherein the mating surface on the sealing lip of the cap is made by means of a tool having a corresponding RMS roughness of at least 0.5 microns.

3. The apparatus of claim 2 wherein the mating surface on the sealing lip of the cap is made by means of a tool having a corresponding RMS roughness of between about 0.5 microns and 50 microns.

4. The apparatus of claim 1 wherein at least one of the first and second mating surfaces is sufficiently roughened to allow gas to escape from the disinfecting chamber when the gas pressure within said disinfecting chamber such that the maximum pressure reached in the lens case is under about 5 psi above atmospheric pressure.

5. The apparatus of claim 1, wherein the disinfecting chamber is capable of venting gas at an internal pressure below 5 psi about atmospheric pressure.

6. The apparatus of claim 1, wherein said subsequent passage means is through the space between the complementary loosely mated threading on the cap and container.

7. The apparatus of claim 1, wherein said apparatus further includes a catalytic component for catalyzing the conversion of a disinfectant into at least one gaseous product.

8. The apparatus of claim 1, wherein said lens holder comprises:

a) a supporting means comprising, convexly shaped projecting lens-shaped surfaces for receiving said contact lenses, and b) a pair of retaining means comprising a pair of baskets which retaining means are pivotally mounted on the supporting means for securing said lenses adjacent said surfaces.

9. A method of forming an apparatus for treating contact lenses, said apparatus including a container and a securable cap, wherein the securing of said cap to said container defines an internal chamber, wherein said mating provides a liquid-impermeable seal for said internal chamber and wherein said apparatus is capable of providing venting to allow excessive gas to vent at a predetermined internal pressure, said method comprising the steps of:

(a) forming a container to receive a peroxide disinfecting solution, said container having a horizontal bottom wall, vertical side walls, and an open end surrounded by an annular rim portion of the side walls;

(b) forming a removable cap affixed to said container at said open end, said cap comprising a sealing lip extending from the inner surface of the cap, which sealing lip comprises a first mating surface overlapping and pressingly engaging with a second mating surface on the annular rim portion of the container when the cap is fully affixed to the container, wherein at least one of the first and second mating surfaces is sufficiently roughened to allow gas to escape from the disinfecting chamber when the internal pressure exceeds a predetermined pressure above atmospheric pressure such that the maximum pressure attained in the lens case is below about 20 psi above atmospheric pressure, and wherein said apparatus further includes a subsequent passage means for allowing gas passing from said disinfecting chamber between said first and second mating surfaces to exit to the environment;

(c) a contact lens holder attached to the inner surface of the cap for retaining a pair of lenses in a submerged location within the apparatus when the cap is affixed to the container.

10. The method of claim 9 wherein the mating surface on the sealing lip is made by means of a tool having a corresponding RMS roughness of at least 0.5 microns.

11. The method of claim 10 wherein the mating surface on the sealing lip is made by means of a tool having a corresponding RMS roughness of between about 0.5 microns and 50 microns.

12. The method of claim 9, wherein either the inside surface of the annular rim portion or the mating surface of the sealing lip is sufficiently roughened to allow gas to escape from the disinfecting chamber when the gas pressure within said disinfecting chamber exceeds a predetermined pressure above atmospheric pressure, such that the maximum pressure reached in the lens case is below about 5 psi above atmospheric pressure.

13. The method of claim 9, wherein the disinfecting chamber is capable of initially venting gas at an internal pressure below 5 psi about atmospheric pressure.

14. The method of claim 9, wherein said subsequent passage means is through the space between the complementary loosely mated threading on the cap and container.

15. The method of claim 9, wherein a catalytic component which catalyzes the conversion of a disinfectant into at least one gaseous product is fixedly attached to the container or the bottom of a lens holder attached to the inside surface of the cap.

16. A method of disinfecting a contact lens with a hydrogen peroxide solution comprising immersing the lens in a solution comprising about 1 to 5 percent of hydrogen peroxide in the presence of a neutralizing agent for a sufficient period of time to disinfect the lenses and neutralize the hydrogen peroxide, which method comprises introducing the solution into a container through an open end, submerging the lens in the solution, and affixing a removable cap to said container at said open end to form a closed disinfection chamber, said cap comprising a sealing lip extending from the inner surface of the cap, which sealing lip comprises a first mating surface overlapping and pressingly engaging with a second mating surface on the annular rim portion of the container when the cap is fully affixed to the container, wherein at least one of the first and second mating surfaces is sufficiently roughed to allow gas to vent from the disinfecting chamber and into a subsequent passageway leading to the environment when the internal pressure exceeds a predetermined pressure above atmospheric pressure, such that the maximum pressure attained in the lens case is below 20 above atmospheric pressure.

17. The method of claim 16, wherein the concentration of peroxide is reduced to less than 100 ppm.

18. The method of claim 16 wherein the sealing lip of the cap is made by means of a tool having a corresponding RMS roughness of at least 0.5 microns.

19. The method of claim 16, wherein the maximum pressure reached in the lens case is below about 5 psi above atmospheric pressure.

20. The method of claim 16, wherein the disinfecting chamber begins to vent gas at an internal pressure below about 2 psi above atmospheric pressure.

* * * * *